United States Patent
Wright et al.

Patent Number: 5,108,382
Date of Patent: Apr. 28, 1992

[54] DISPOSABLE CONTAINERS

[75] Inventors: John R. Wright, Loxwood; Bruce Samways, Bleadon, both of United Kingdom

[73] Assignee: Timbale Corporation NV, Netherlands

[21] Appl. No.: 754,222

[22] Filed: Aug. 27, 1991

Related U.S. Application Data

[63] Continuation of Ser. No. 449,062, Dec. 18, 1990, abandoned, which is a continuation of Ser. No. 275,633, Nov. 16, 1988, abandoned, which is a continuation of Ser. No. 60,994, Jun. 5, 1987, abandoned, which is a continuation of Ser. No. 774,387, Sep. 10, 1985, abandoned, which is a continuation of Ser. No. 679,614, Dec. 10, 1984, abandoned, which is a continuation of Ser. No. 479,931, Mar. 29, 1983, abandoned, which is a continuation-in-part of Ser. No. 292,177, Aug. 12, 1981, abandoned.

[30] Foreign Application Priority Data

Aug. 12, 1980 [GB] United Kingdom ............... 8026275
Mar. 31, 1982 [GB] United Kingdom ............... 8209526

[51] Int. Cl.$^5$ .................................. A61F 5/44
[52] U.S. Cl. .................................. 604/342; 604/332
[58] Field of Search ............... 604/317, 332–345, 604/366, 372; 428/35, 518

[56] References Cited

U.S. PATENT DOCUMENTS

| | | | |
|---|---|---|---|
| 3,089,493 | 5/1963 | Galindo | 604/342 |
| 3,403,064 | 9/1968 | Bellamy | 383/113 |
| 3,559,650 | 2/1971 | Larson | 128/290 |
| 3,613,123 | 10/1971 | Langstrom | 604/339 |
| 3,651,809 | 3/1972 | Champaigne, Jr. | 128/290 |
| 3,654,064 | 4/1972 | Lauman | 4/DIG. 18 |
| 3,763,502 | 10/1973 | Lauman | 4/DIG. 18 |
| 3,902,496 | 9/1975 | Eakin | 604/334 |
| 3,926,233 | 12/1975 | Brendling | 604/335 |
| 3,934,587 | 1/1976 | Gordon . | |
| 3,952,347 | 4/1976 | Comerford et al. | 128/284 |
| 4,185,630 | 1/1980 | Neumeier | 604/344 |
| 4,254,008 | 3/1981 | Krsek | 604/336 |
| 4,326,521 | 4/1982 | Marsan | 128/283 |
| 4,343,053 | 8/1982 | O'Connor | 4/452 |

FOREIGN PATENT DOCUMENTS

| | | | |
|---|---|---|---|
| 653680 | 5/1951 | United Kingdom . | |
| 1127438 | 9/1968 | United Kingdom . | |
| 1312370 | 4/1973 | United Kingdom . | |
| 1579919 | 11/1980 | United Kingdom . | |
| 2083762 | 3/1982 | United Kingdom | 604/332 |

OTHER PUBLICATIONS

WO 80/01374, Jul. 1980, WIPO.

*Primary Examiner*—Randall L. Green
*Assistant Examiner*—R. Clarke
*Attorney, Agent, or Firm*—Sherman and Shalloway

[57] ABSTRACT

A water closet-disposable container is disclosed, the container having a wall comprising a backing layer, an inwardly-presented water-impermeable layer and an outer wall formed of a material having characteristics similar to those of the backing layer. The container is formed by sealing together juxtaposed marginal edge portions of the water impermeable layer, and the projecting marginal edge portions of the backing layer and the outer wall.

9 Claims, 1 Drawing Sheet

DISPOSABLE CONTAINERS

This application is a continuation of application Ser. No. 07/449,062, filed De. 18, 1990 which is a continuation of Ser. No. 07/275,633, (Nov. 16, 1988); continuation of Ser. Mo. 060,994 (June 5, 1987); continuation of Ser. No. 774,387 (Sept. 10, 1985) continuation of Ser. No. 679,614 (Dec. 10, 1984); continuation of Ser. No. 479,931 (Mar. 29, 1983); continuation-in-part of Ser. No. 292,177 (Aug. 12, 1981) all abandoned.

BACKGROUND OF THE INVENTION

This invention relates to containers for receiving bodily excretions and which are readily disposable in a water closet.

Bodily excretions such as feces, urine and sputum are either collected in washable and re-usable containers or in disposable containers. There is wide use of disposable containers when the excretions are being collected for disposable, such as in the use of disposable bedpans or in the use of disposable containers by incontinent patients or by patients who have undergone colostomy, ileostomy or urostomy (hereinafter referred to as "ostomy patients"); and when the excretions are being collected as samples, for example as urine samples. Such disposable containers may readily be made from hydrophobic heat-sealable flexible films of, for example, polyethylene, EVA or PVC, but are not then disposable via a WC as they tend either to float, due to entrapped air and to the low specific gravity of such materials and are therefore not carried away when the WC is flushed; or, if they are carried away, tend subsequently to cause drain blockage.

European Patent Application No. 0 010 171 discloses a WC-disposable container or sachet for receiving bodily excretions fabricated from a three-layer sheet material, the first layer which is inwardly presented being of water-insoluble material, for example polyethylene, the second, supporting or backing layer being of water-soluble material, for example polyvinyl alcohol, and the third, outer layer being of water-insoluble, but water-disintegrated, material such as kraft paper which allows the wearer's skin to breathe and protects the intermediate layer from excessive sweat. On being placed after use in a WC the outer layer disintegrates and the intermediate layer dissolves, leaving the unsupported layer to be broken up under the flushing action of the WC and thus enabling the container and its contents to be flushed away. Such a container is formed by sealing together only the juxtaposed marginal edge portions of the inwardly-presented layers. As the layers cannot be intrinsically strong if they are to disintegrate under the flushing action when unsupported by the backing layer, and are not usually strongly bonded thereto, a source of structural weakness is introduced.

Containers that may be disposed of in a WC without the disposer's being fouled by, or even coming into contact with, the contents and having improved edge seals are described in our UK Application No. 2 083 762 A, which was not published before the priority date of the present Application which relates to such containers having further improved structural properties.

SUMMARY OF THE INVENTION

According to the present invention there is provided a WC-disposable container, for example an ostomy or incontinence bag, having a wall comprising a backing layer formed of a material which has good tensile strength and cohesion when dry but is dissoluble or dispersible in mildly turbulent water, and an inwardly-presented water-impermeable layer which has low intrinsic cohesion and acts as a water barrier only so long as its integrity is maintained by the backing layer and is disintegrated when the backing layer is dispersed or dissolved by immersion in a flushed WC, the container being formed by sealing together juxtaposed marginal edge portions of the water-impermeable layer of wall-forming sheet material, characterised in that the container additionally comprises at least one outer wall formed of material having characteristics similar to those of the backing layer and having marginal edge portions which project beyond those of the water-impermeable layer, and in that the respective portions of the outer-wall-forming material overlying the marginal edge portions of the backing layer are sealed thereto, and that the projecting marginal edge portions of the outer-wall-forming material are sealed together.

The use of at least one layer of outer-wall-forming sheet material having the projecting marginal edge portions sealed together to form an integral or united outer wall not only provides an edge seal having the extra mechanical strength afforded by the use of the overlapping edge strips described in parent application Ser. No. 06/292,177, filed Aug. 12, 1981, now abandoned, but also provides a stronger container overall because, thickness for thickness, a multi-walled container is stronger than a single-walled container. Moreover a panel of material is easier to handle in manufacture than separate strips, particularly when the edges of the container are not rectilinear.

The material of the backing layer forming the inner wall, and of the outer wall or walls, is preferably heat-sealable; and is preferably the same material, for example polyvinyl alcohol (PVOH). The material of the inner, water-impermeable layer is desirably also heat-sealable but may be of a self-adhesive material forming a bond which is not affected by heat-sealing.

The container may in some cases be fabricated from a single, folded panel of inner- and outer-wall forming material, but is preferably fabricated from two sets of panels which are sealed together around the whole length of their marginal edge portions.

The backing layer material is preferably a plastics film and the water-impermeable layer formed as a coating on the backing layer. The term 'film' is defined as a homogeneous structure having smooth surfaces and 'coating' as a homogeneous continuous layer which maintains its integrity when supported on a suitable backing layer. Examples of suitable plastics film materials for forming the backing layer are polyethylene oxide and even more suitable, PVOH, as previously mentioned, preferably 25 μ (0.001") to 38 μ (0.0015") thick, on account of its excellent resistance to the diffusion of oxygen and odours therethrough, its ability to provide a good barrier to bacteria, and its not making a possibly embarrassing noise when flexed. Moreover, PVOH may be plasticised to a desired degree of flexibility and hydroscopicity, for example by the use of a mixture of polyethylene glycol and polyester polyol in an amount of from 5 to 25% by weight of the PVOH or glycerol in an amount of from 10% to 20%, preferably 12 to 15%, and formulated to have a desired degree of solubility: for example a hot-water-soluble grade will remain coherent for longer than a cold-water-soluble grade if partially wetted accidentally, but still be broken up in a flushed WC and completely dissolved in the drain.

Suitable materials for forming a water-impermeable coating layer are polyvinylidene chloride (PVDC), vinyl chloride-vinylidene chloride copolymer (SARAN-Trade Mark), atactic polypropylene, nitrocellulose, waxes, greases, silicones and pressure-sensitive adhesives, for example a solution of a rubber latex in an organic solvent; however the choice of materials is wide and, moreover, the water-impermeable layer may be formed, not by coating the backing layer, but by a film which is adhered to the backing layer.

Examples of suitable coating thicknesses are 3 to 10 g/m² for SARAN, PVDC and plasticised nitrocellulose coating, 5 to 6 g/m² for a latex coating and 5 to 30 g/m² for a cold-sealing adhesive coating.

If the outer wall is constituted by a single layer of material this is preferably 50 $\mu$ (0.002") thick; where it is constituted by two layers each may be of half this thickness.

The nature of the water-impermeable layer makes the material difficult to handle during fabrication of the container and renders it liable to become damaged; moreover juxtaposed areas of the water-impermeable layer tend to stick together, a difficulty encountered both during fabrication and with the finished container. According to a further aspect of the present invention these difficulties are overcome by additionally supporting and protecting the water-impermeable layer, on the face remote from the backing layer, with a further layer of a material such as may be used for forming the backing layer. Naturally, on exposure to water, that present for example in urine, the further layer dissolves or weakens, its function as a barrier between juxtaposed surfaces of the water-impermeable layer being taken over by the water to which it was exposed. The use of a further layer allows the water-impermeable layer to be applied to the backing layer as a highly plasticised coating; and, should the coating have been applied in the solvent phase, prevents blocking if the solvent has not been completely evaporated. Another advantage deriving from the presence of the further layer is that such a sandwich-like material (in which the backing and further layers correspond to the bread and the water-impermeable layer to the filling) may be formed by bringing together the water-impermeable layers coated onto separate sheets of backing material; the integrity against pin-holes of the water-barrier so formed from the combination of two coated layers is thus guaranteed.

A container for certain applications may conveniently be formed of a sheet material in which the water-impermeable layer is constituted by a pressure-sensitive, non-heat-degradable adhesive, for example the hot-melt pressure-sensitive adhesive sold by Beardow Adams, Ltd., under the designation BAE 124 coated in an amount of 5 to 30 g/m².

The container according to the present invention may be of any suitable shape, for example rectangular or the conventional inverted flask shape and when intended to be used as an ostomy bag the container is provided with an access port and suitable means for connecting the container to a patient, for example an adhesive coated area surrounding the port or a ring of water-soluble or water-dispersible material co-operating with another ring adhesively secured to the patient.

Whilst a container according to the present invention is adequately strong for normal use, the extremely high level of confidence which an ostomy patient expects to have in his container may be enhanced if the disposable container is mechanically supported externally by being placed within a conventional flexible water-proof container of hydrophobic material. Accordingly such a combination of a WC-disposable container and a conventional container constitutes a still further aspect of the present invention.

As the containers according to the present invention are readily disposable they are usually closed-bottom containers which obviate the need for the messy emptying operation that is necessary to prolong to an economical period the life of a conventional container having a re-sealable opening at the lower end.

Although the invention may be carried out in a great variety of ways, one particular embodiment thereof will now be described, by way of example, with reference to the accompanying drawings in which

BRIEF DESCRIPTION OF THE PREFERRED DRAWINGS

FIG. 3 shows a cross sectional view showing an access port. FIG. 3 is a part-section through an access port according to the present invention.

SPECIFIC DESCRIPTION OF THE PREFERRED EMBODIMENTS

Figure 1:
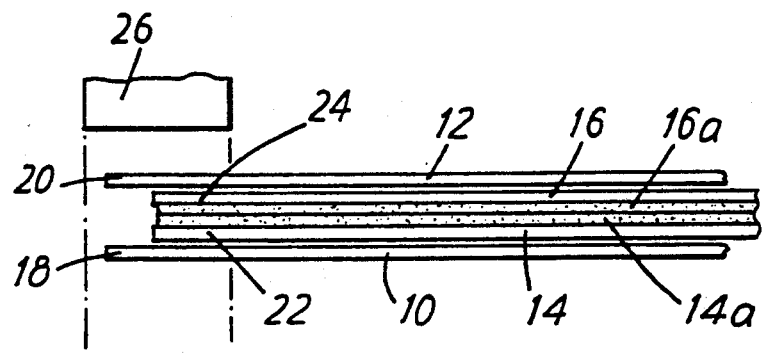
FIG. 1 is a part-section through a stack of panels of sheet material before edge-sealing to form an ostomy pouch according to the present invention.

An ostomy pouch according to the embodiment is fabricated in the following manner.

Two outer-wall-forming panels 10, 12 are cut from PVOH sheet 50 $\mu$](0.002") thick and two slightly smaller inner-wall forming panels 14, 16 are cut from PVOH sheet, 25 $\mu$ (0.001") thick, previously coated with a thin film of PVDC 14a, 16a.

An access port 13 injection-moulded from PVOH and having a basal flange 13a is passed through an aperture in the panel 12 and the basal surface of the flange heat sealed to the panel 16 and its other surface to the panel 12. The inner face of the annulus 13 and the exposed edge of the PVDC film 16a are coated with PVDC.

The panels 10, 12, 14, 16 are stacked as shown in FIG. 1 with the panels 10, 12 on the bottom and top of the stack respectively and with their respective marginal edge portions 18, 20 projecting beyond the marginal edge portions 22, 24 of the inner panels 14, 16 which are sandwiched therebetween with their coated films 14a, 16a facing but separated by an inset slip sheet (not shown).

Figure 2:
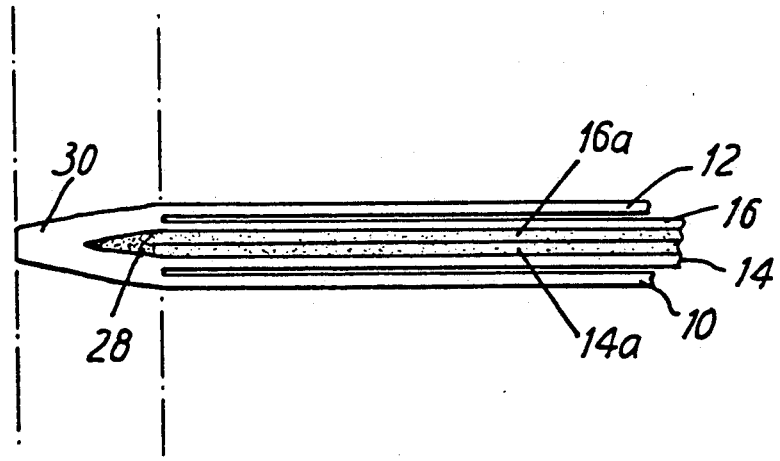
FIG. 2 is a similar section showing the panels after sealing.

When a sealing iron 26 is operated the PVDC films 14a, 16a are welded together at 28 (see FIG. 2) in the area of the marginal edge portions 22, 24; in the corresponding area the panel 10 is welded to the panel 14 and the panel 12 to the panel 16, and the marginal edge portions 18, 20 of the outer panels 10, 12 are welded to each other to form the welded portion shown at 30. The very strong edge-seal shown in FIG. 2 is thus created.

In an alternative embodiment a pouch is fabricated from a pair of outermost, preferably rectangular, panels of PVOH film, a slightly smaller intermediate pair of similarly-shaped panels of PVOH having a water-impermeable coating (with the coating facing inwardly) and an innermost pair of still slightly smaller panels of the same coated PVOH (with the coating facing outwardly).

A correspondingly shaped heat seal is then used to seal together the outer margins of the outermost pair of panels to give a welded PVOH surface around the periphery; to seal together the marginal portions of the coatings on the intermediate pair of panels; and to seal together the respective overlying portions of the PVOH outermost and intermediate panels. The juxtaposition of the coated surfaces of the inner and intermediate layers gives a double thickness water-impermeable coating which provides an additional safeguard against pinholes.

The innermost pair of panels which effectively constitute slip sheets may alternatively be formed from cellulose film having a water-soluble coating on one face thereof. Such a coated film is cheap, being commercially available; forms an excellent water-barrier; and, it has been discovered, is silent when adhered to the adjacent coated PVOH panel. The rigidity of the cellulose film also facilitates pouch construction and the heat-sealing operation.

It will be appreciated that one of the great benefits afforded by the above-described embodiments is the provision of a container having an integral outer surface.

What is claimed is:

1. A water closet disposable ostomy bag comprising: walls, each having an outer edge, formed of a composite sheet material comprising an outwardly presented backing layer composed of a material which is cohesive when dry but which is dissolved or dispersed when immersed in moving water produced on flushing of a water closet and an inwardly presented layer composed of a water-impermeable material which is mechanically disintegratable after said outwardly presented backing layer is dispersed or dissolved during said flushing, said two walls being heat sealed together at said outer edges with said inwardly presented layers facing each other;
an aperture defined by an opening in one of said walls; and
an access port, comprising a water-closet disposable annulus, disposed in said aperture and bonded to said one of said walls proximate said aperture, said access port providing means of connection to a stoma of a patient, said access port being dissolved or dispersed after being immersed in moving water produced on flushing of a water closet.

2. The bag as claimed in claim 1, wherein said inwardly presented layer has marginal edge portions and said backing layer has corresponding marginal edge portions which extend beyond said marginal edge portions of said inwardly presented layer, said marginal edge portions of said inwardly presented layer being sealed together and said corresponding marginal edge portions of said backing layer being sealed together.

3. The bag as claimed in claim 1, wherein said inwardly presented layer is a plastics film adhered to said backing layer.

4. A water closet disposable ostomy bag comprising:
an inner wall;
at least one outer wall;
an aperture defined by an opening formed in at least said at least one outer wall; and
an access port, comprising a water closet disposable annulus having an inner face, mounted over said aperture and providing means of connection to a stoma of a patient; wherein: said inner wall comprises a backing layer formed of a material which is cohesive when dry but which is dissolved or dispersed when immersed in moving water produced on flushing of a water closet and an inwardly presented layer, formed of a water-impermeable, which acts as a water barrier only so long as its integrity is maintained by the backing layer and is disintegrated after the backing layer is dispersed or dissolved by immersion in a flushed water closet,
said outer wall formed of a material which is cohesive when dry but which is dissolved or dispersed when immersed in moving water produced on flushing of a water closet,
said inwardly presented layer having marginal edge portions, said backing layer having first corresponding marginal edge portions and said at least one outer wall having second corresponding marginal edge portions which extend beyond said marginal edge portions of said inwardly presented layer, said marginal edge portions of said inwardly presented layer being sealed together and said second corresponding marginal edge portions of said at least one outer wall being sealed to said first corresponding marginal edge portions of said backing layer,
said access port being dissolved or dispersed when immersed in moving water produced on flushing of a water closet, said inner face coated with said water-impermeable material.

5. The bag as claimed in claim 4, wherein said inwardly presented layer is a plastics film adhered to said backing layer.

6. The bag as claimed in any one of claims 1, 2, 4 or 5, wherein said inwardly presented layer is formed from a material selected from the group consisting of polyvinylidene chloride, vinyl chloride-vinylidene chloride copolymer, atactic polypropylene, nitrocellulose, waxes, greases, silicones, rubber latexes, acrylic latexes, and cold-sealing, hot-melt pressure-sensitive adhesive.

7. The bag as claimed in any one of claims 1, 2, 4 or 5, wherein said backing layer material is selected from the group consisting of polyethylene oxide film and polyvinyl alcohol film.

8. The bag as claimed in claim 7, wherein said backing layer material has a thickness of from 25 to 75 $\mu$.

9. The bag as claimed in any one of claims 1 or 4, wherein said access port is formed of polyvinyl alcohol.

* * * * *